United States Patent
Kierath

(10) Patent No.: US 10,485,686 B2
(45) Date of Patent: Nov. 26, 2019

(54) INTRAGASTRIC BALLOON

(71) Applicant: SIMPLE MEDICAL INNOVATIONS PTY LTD, City Beach, WA (US)

(72) Inventor: Thomas Kierath, City Beach (AU)

(73) Assignee: SIMPLE MEDICAL INNOVATIONS PTY LTD, City Beach (AU)

(*) Notice: Subject to any disclaimer, the term of this patent is extended or adjusted under 35 U.S.C. 154(b) by 670 days.

(21) Appl. No.: 14/422,020

(22) PCT Filed: Jul. 24, 2013

(86) PCT No.: PCT/AU2013/000826
§ 371 (c)(1),
(2) Date: Feb. 17, 2015

(87) PCT Pub. No.: WO2014/026215
PCT Pub. Date: Feb. 20, 2014

(65) Prior Publication Data
US 2015/0216697 A1 Aug. 6, 2015

(30) Foreign Application Priority Data
Aug. 17, 2012 (AU) ................................ 2012903567

(51) Int. Cl.
*A61F 5/00* (2006.01)
(52) U.S. Cl.
CPC ............ *A61F 5/0036* (2013.01); *A61F 5/003* (2013.01)

(58) Field of Classification Search
CPC ... A61F 5/0036; A61F 5/003; A61B 17/12136
See application file for complete search history.

(56) References Cited

U.S. PATENT DOCUMENTS

| 5,129,915 | A | 7/1992 | Cantenys |
|---|---|---|---|
| 2004/0186502 | A1 | 9/2004 | Sampson et al. |
| 2010/0100115 | A1* | 4/2010 | Soetermans .......... A61F 5/0036 606/192 |
| 2010/0215732 | A1* | 8/2010 | Mintchev ............. A61F 5/0036 424/451 |
| 2012/0232576 | A1* | 9/2012 | Brister .................. A61F 5/0013 606/192 |

FOREIGN PATENT DOCUMENTS

| EP | 0103481 | 3/1984 |
|---|---|---|
| WO | 2011136745 | 11/2011 |

OTHER PUBLICATIONS

International Search Report dated Oct. 11, 2013 from International Application No. PCT/AU2013/000826, pp. 1-5.

* cited by examiner

*Primary Examiner* — Julie A Szpira
(74) *Attorney, Agent, or Firm* — MH2 Technology Law Group, LLP

(57) ABSTRACT

An intragastric balloon (10) for use in the stomach including a sealed container and separated expandable foaming substances within the sealed container, wherein the substances are adapted to expand and cure to a foam when mixed.

20 Claims, 7 Drawing Sheets

INTRAGASTRIC BALLOON

CROSS-REFERENCE TO RELATED APPLICATIONS

This application is a U.S. National Stage application of PCT/AU2013/000826 filed 24 Jul. 2013, which claims priority to Australian patent application 2012903567 filed 17 Aug. 2012, the entire disclosures of which are hereby incorporated by reference in their entireties.

TECHNICAL FIELD

The present invention generally relates to intragastric balloons for obesity treatment.

BACKGROUND ART

Intragastric balloons as an alternative to obesity treatment using drugs, behavior therapy, physical exercise and surgery are well known. For some time physicians have been placing intragastric balloons into the stomach reservoir to reduce the available area within the stomach and hence limit capacity for food. Once deployed in the stomach and expanded to its full size, the balloon helps to trigger a sensation of fullness and a decreased feeling of hunger. These prior art balloons are typically spherical, cylindrical or pear shaped, generally range in size from 200-700 ml or more, are made of an elastomer such as silicone, polyurethane, or latex, and are filled with air, water, or saline.

These prior art balloons are often inserted into the stomach in an deflated state via endoscope or swallowing and are then inflated with gas, liquid and sometimes foam using a tube passing through the mouth and oesophagus that actively inflates or expands the balloon. Other balloons include a tube exiting the nasal passage that allows the balloon to be periodically deflated and re-inflated to better simulate normal food intake. The need to inflate and/or deflate the balloon in the stomach can cause significant discomfort to the patient. Alternatively these prior art balloons can be inserted surgically and inflated during the surgery procedure. In all these arrangements the need to seal the intragastric balloon once it has been inflated or deflated arises.

With endoscopic oesophageal insertion and subsequent inflation and/or deflation or with surgical insertion there are inherent risks to the patient, some of these being perforation of the oesophagus and/or stomach, leakage or spillage of the material to be injected into the balloon and standard risks associated with anesthetic.

Some prior art intragastric balloons require gastric fluid to pass through the external wall of the balloon, causing material within it to expand due to added liquid. In these prior art balloons gastric fluid is able to continuously interact with the material within the balloon.

With the use of these prior art gastric balloons complications have also been observed, such as gastric ulcers, and small bowel obstructions caused by deflated balloons. In addition, there have been documented instances of the balloon blocking off or lodging in the opening to the duodenum, wherein the balloon may act like a ball valve to prevent the stomach contents from emptying.

The preceding discussion of the background art is intended to facilitate an understanding of the present invention only. The discussion is not an acknowledgement or admission that any of the material referred to is or was part of the common general knowledge as at the priority date of the application.

SUMMARY OF INVENTION

The present invention seeks to provide an intragastric balloon that overcomes or ameliorates at least some of the problems referred to above, or to at least reduce the likelihood of at least one of the difficulties referred to above arising.

The present invention provides a self expanding intragastric balloon for use in the stomach including a sealed container and separated expandable foaming substances within the sealed container, wherein the substances are adapted to expand and cure to a foam when mixed, and wherein the foam, when cured, substantially fills the intragastric balloon.

In a second aspect of the present invention, there is provided a self expanding intragastric balloon for use in the stomach including a sealed container and separated expandable foaming substances within the sealed container, wherein the substances are adapted to expand and cure to a foam when mixed; and wherein material that the balloon is made of promotes transfer, through the material, of the gas created when the mixture expands and cures to a foam so that the foam, when cured, substantially fills the intragastric balloon.

The expanding of the foam may be timed so that the substances are mixed out of the body and the intragastric balloon swallowed before the intragastric balloon is fully expanded.

The intragastric balloon may be too large to pass through the pyloric sphincter once the substances are cured.

The substances may be separated by a frangible membrane.

The substances may be separated by a clip.

Before the substances are cured the intragastric balloon may be swallowed.

The volume of the intragastric balloon before the substances have expanded may be between 1 ml and 25 ml.

The intragastric may be compressed prior to the substances being cured.

The intragastric balloon may be compressed by folding.

The intragastric balloon may be compressed by rolling.

The substances may be selected from polydimethyl siloxanes, polyurethanes and poly siloxanes.

The sealed container may be made from polydimethyl siloxane, polytetrafluro ethylene, poly ethylene, low density polyethylene, poly propolyene, polyester and poly amide.

The intragastric balloon may include a removal device attached to the sealed container adapted to communicate the intragastric balloon with the outside environment when the intragastric balloon is passing into the stomach.

The volume of the intragastric balloon after the expandable substances have cured may be between 50 ml and 700 ml.

Gas transportation of gases produced within the intragastric balloon and atmospheric gases may be approximately equal.

The substances may be mixed using a baffle mixer.

Once the foam has cured, the intragastric balloon may be adapted to maintain its shape if punctured.

In a third aspect of the present invention, there is provided a self expanding intragastric balloon for use in the stomach including a sealed container and separated expandable foaming substances within the sealed container, wherein the substances are adapted to expand and cure to a foam when mixed, and wherein there is no space between the sealed container and the foam after the foam has expanded.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIG. 6b is an end view of the intragastric balloon of FIG. 6a;

In the drawings like structures are referred to by like numerals throughout the several views. The drawings shown are not necessarily to scale, with emphasis instead generally being placed upon illustrating the principles of the present invention.

DESCRIPTION OF EMBODIMENTS

The obesity treatment apparatus depicted in FIG. 1-13 of the present invention comprises one or more balloons, each comprising an inert outer skin filled with a separated self foaming compound, that once activated expands to fill the void within the balloon. Once within the gastric lumen of a mammalian patient the device will reside therein and be generally unable to pass through the pylorus to enter the duodenum. As used herein, the term foam material is intended to refer to a material used to expand and occupy volume within the intragastric balloon and outer skin is the balloon material which is generally not subject to the degradative effects of stomach acid and enzymes or the general environment found within the gastric system over an extended period of time therefore allowing the device to remain intact for the intended life of the device. However this does not necessarily mean that the foam and or skin material cannot be degraded over time.

Figure 1:
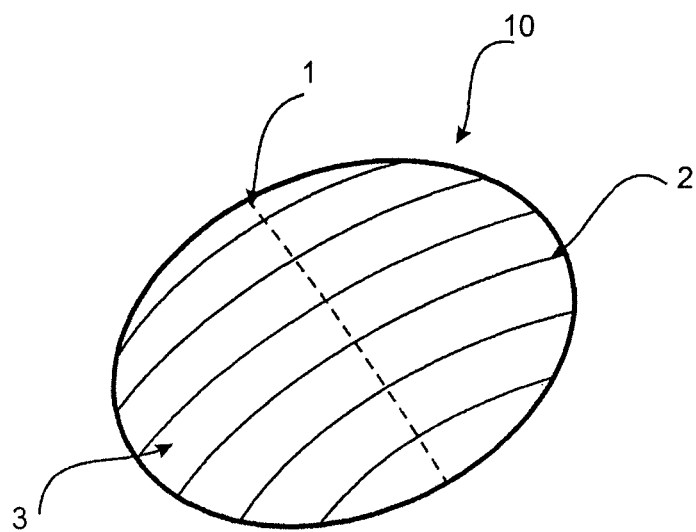
FIG. 1 is a perspective view of an intragastric balloon according to a first embodiment of the present invention.

FIG. 1 depicts a first embodiment of an intragastric balloon 10 according to the present invention in its pre-expanded stage. The intragastric balloon 10 is a preformed sealed device that includes a first region 2 and a second region 3 separated by a frangible internal membrane 1. The first and second regions 2 and 3 hold two foamable precursors that are separated by the membrane 1. The foamable precursors can be inserted into the intragastric balloon 10 at the time of the balloons manufacture, or an alternatively be inserted after manufacture through sealable openings in the balloon body. The intragastric balloon 10 can be made of a material resistant to the effects of the gastric environment such as linear low density polyethylene, Polydimethyl siloxane, polytetrafluro ethylene, Poly ethylene, poly propylene, and poly amide. The foamable precursors can include but are not limited to foamable Polydimethyl siloxane, polyurethanes and other poly siloxanes capable of foaming.

When frangible membrane 1 is broken, the two foamable precursors are mixed and the foamable precursors begin to activate and expand. On activation the precursors begin to polymerize, foam, expand and cure into a stable foam material that remains expanded within the walls of the intragastric balloon 10 when cured. The cured expanded foam substantially fills the intragastric balloon 10 so that the outer surface of the expanded foam abuts the inner wall of the intragastric balloon 10. The stable foam material can also maintain its expanded shape if it were to be directly exposed to the gastric environment. This can ensure that if the walls of the intragastric balloon are punctured, the device will maintain its shape and will not be drawn into the pyloric sphincter. Additionally a dye agent may be included in the foamable precursors such that if the device is punctured said dyeing substance will be released from the device into the gastrointestinal tract, said dye may be selected to make noticeable changes to the colour of the patients stool, urine or sclera. Biocompatible dyes such as methylene blue are suitable for this use. If the foamable precursors are Polydimethyl siloxane the foam is formed through the simultaneous release of hydrogen gas and solidification of the Polydimethyl siloxane polymer.

One possible method of activation is through the application of an external force. For example the membrane 1 can be ruptured by physical manipulation of the intragastric balloon 10. For example, through the use of the rollers illustrated in FIGS. 3a and 3b. Alternative forms of activation can include temperature, light, PH or a combination of forms that can break the frangible membrane 1 as understood by the skilled addressee. Once activated, the intragastric balloon 10 can initially expand slowly, expanding to full size within 15 minutes. When expanded to full size, the intragastric balloon 10 will be of sufficient size to prevent it passing through the pyloric sphincter. Fully expanded the intragastric balloon 10 can have a width of at least 5 cm and an expanded volume of between 50 ml to 250 ml.

In one embodiment the intragastric balloon 10 will be made of a polymer material that has flexibility, stability when immersed in acid and controlled gas transport, such as low density polyethylene. When a byproduct of the expansion of the foamable precursors is hydrogen gas the gas transportation qualities of the polymer material limit the transportation of hydrogen gas produced in the foaming process compared to that of atmospheric gases (Nitrogen, Oxygen, Water Vapour and Carbon Dioxide). By regulating the transportation of hydrogen gas to be generally evenly matched to that of atmospheric gases the pressure within the balloon remains generally constant due to the hydrogen escaping from the intragastric balloon 10 being closely matched by the atmospheric gas entering it and the balloon maintains its intended shape.

Figure 2:
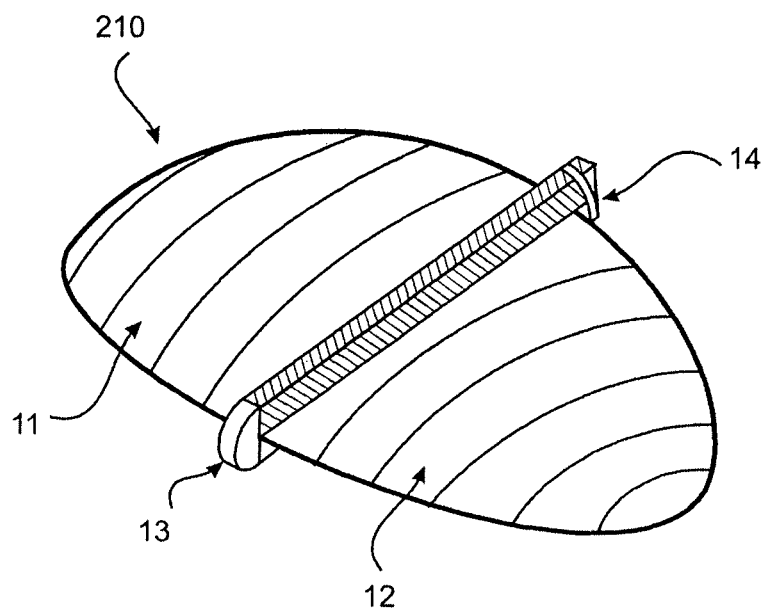
FIG. 2 is a perspective view of an intragastric balloon according to a second embodiment of the present invention.

FIG. 2 illustrates a similar spherical embodiment of the intragastric balloon 210 as illustrated in claim 1 using a different method to separate the foamable precursors. The foamable precursors are separated into different sections 11 and 12 and a mechanical form of separation, external clip 13, is illustrated as separating the two or more foamable precursors. The clip 13 can have a releasable attachment mechanism at one end 14, which once undone allows the clip 13 to be removed. Alternatively, the mechanical form of separation can be a snap seal or otherwise.

Figure 3A:
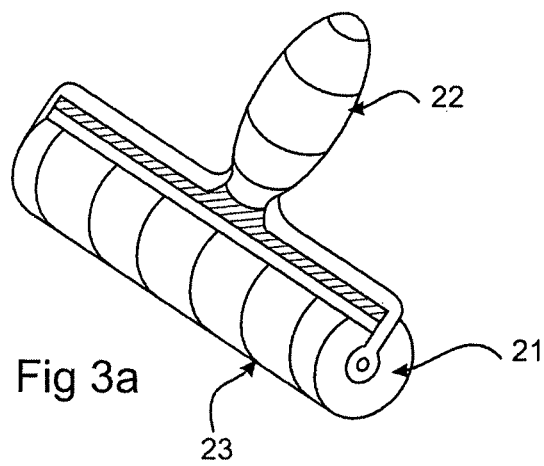
FIG. 3a is a perspective view of a roller for activating the intragastric balloon of FIG. 1 or 2.

FIG. 3a depicts a roller that may be used to activate the balloon where an internal separation device such as membrane 1 is used. The roller includes a handle 22 and roller drum 21 with a smooth roller drum surface 23. The roller drum surface 23 can be rolled over the membrane 1 to apply the require force to rupture the membrane and allow the foamable precursors to mix and activate.

Figure 3B:
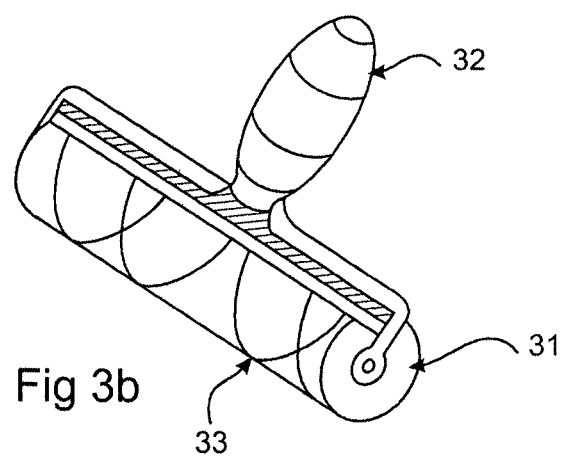
FIG. 3b is a perspective view of an alternative roller for activating the intragastric balloon of FIG. 1 or 2.

FIG. 3b illustrates an alternative embodiment of FIG. 3a's roller including handle 32 and roller 31. The roller surface 33 includes multiple groves that intersect to enhance the mixing action of the roller.

Figure 4:
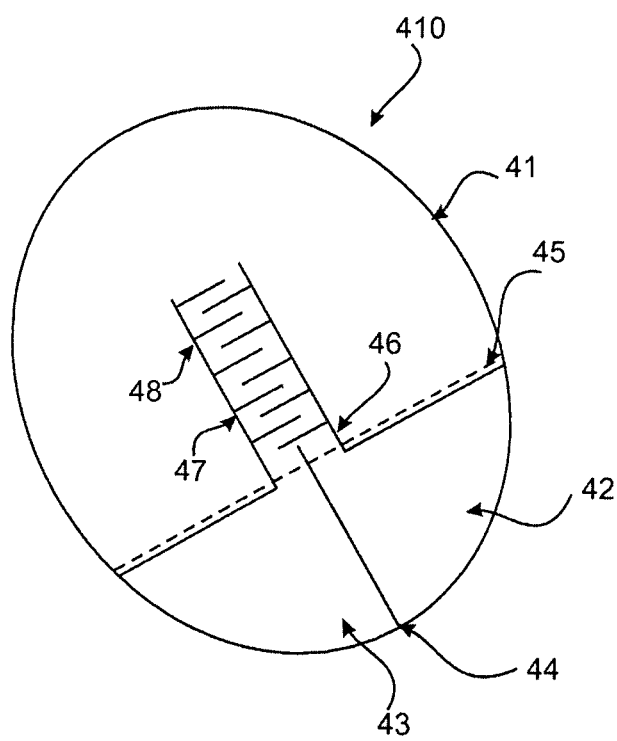
FIG. 4 is a perspective view of an intragastric balloon according to a third embodiment of the present invention.

FIG. 4 illustrates an alternative embodiment of the intragastric balloon 410 in its pre-activated form where a baffle mixer 48 is used. The foamable precursors are located in regions 42 and 43, separated by an internal barrier section 44. The barrier section 44 can be a permanent fixture or a frangible barrier. A membrane 46 or a means of external mechanical separation such as a clip or clips along line 45 is employed to keep the two or more foamable precursors separate prior to activation of the balloon. The intragastric balloon 410 can be activated by breaking the membrane 46 or removing the external mechanical separation 45, depending on which is present. Upon activation, the two foamable precursors are forced through the baffle mixer 48 by an external force. Having passed through the baffle mixer the foamable precursors are adequately mixed and become dispersed within the main volume of the balloon 41 to activate, expand and cure into an expanded foam.

Figure 5:
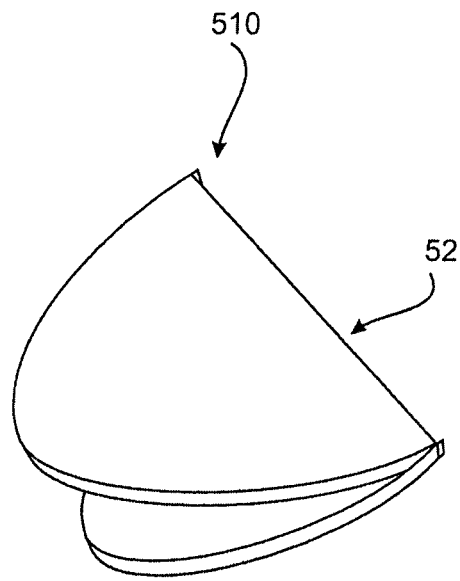
FIG. 5 is a perspective view of an initial form of the intragastric balloon of FIG. 1, 2 or 4 before expansion.
Figure 6A:
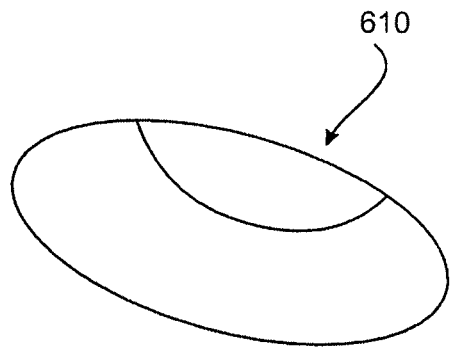
FIG. 6a is a side view of the intragastric balloon of FIG. 1, 2 or 4 prepared for ingestion.
Figure 6B:
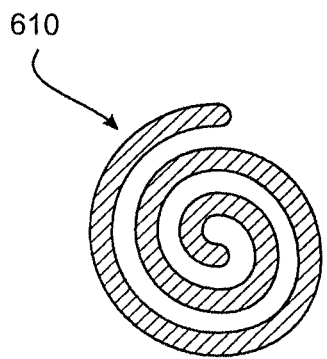

FIGS. 5, 6a and 6b illustrate arrangements for any of the above mentioned embodiments of the intragastric balloon 510, 610 that facilitates passing of the pre-expanded intragastric balloon 510, 610 through the oesophagus. The intragastric balloon 510, 610 is manipulated to make a more compact shape to facilitate passage through the oesophagus. When a more compact shape is achieved the intragastric balloon 510, 610 can be swallowed if the compact shape is of sufficiently small size, or inserted endoscopically otherwise. To more readily enable swallowing of the intragastric balloon 510, 610, the volume of the unexpanded foamable precursor within the intragastric balloon 510, 610 can be between 1 ml and approximately 25 ml. When endoscopic insertion is used a larger intragastric balloon 510, 610 can be used capable of holding larger volumes of the unexpanded foamable precursor.

FIG. 5 illustrates the intragastric balloon 510 as folded along its central axis 52 to reduce the width of the intragastric balloon 510, resulting in a more compact shape that is more readily passed through the oesophagus. Alternatively the intragastric balloon 510 can be folded in three, four or in other arrangements readily understood by the skilled addressee.

FIGS. 6a and 6b illustrate the side and end views respectively of a particular arrangement of any of the embodiments of the intragastric balloons described above in a compact arrangement where the intragastric balloon is rolled along the centre axis. The side view in FIG. 6a illustrates the ellipsoid shape that can be taken by the rolled balloon. FIG. 6b is an end view illustrating how the balloon is rolled to achieve this shape. These are only two of many possible arrangements for making the balloon more compact and the skilled addressee would readily recognize alternative arrangements.

As mentioned above, the time taken from activation of the intragastric balloon to when the intragastric balloon has fully expanded can be up to 15 minutes. Limiting the time taken for the expansion of the intragastric balloon aids in ensuring that the intragastric balloon can be swallowed or endoscopically inserted in the stomach lumen while relatively small, but will also expand quickly enough to ensure that the intragastric balloon does not pass through the pyloric sphincter into the duodenum. The speed of the intragastric balloon's expansion can be controlled through the addition of catalysts in the foamable precursor such as platinum catalysts, through controlling the temperature of the intragastric balloon so that it is chilled at the time of activation and insertion into the stomach lumen. By chilling the balloon or controlling the amount of catalyst in the foamable precursors, the rate of foam production and curing can be delayed to ease passage through the oesophagus.

Figure 7:
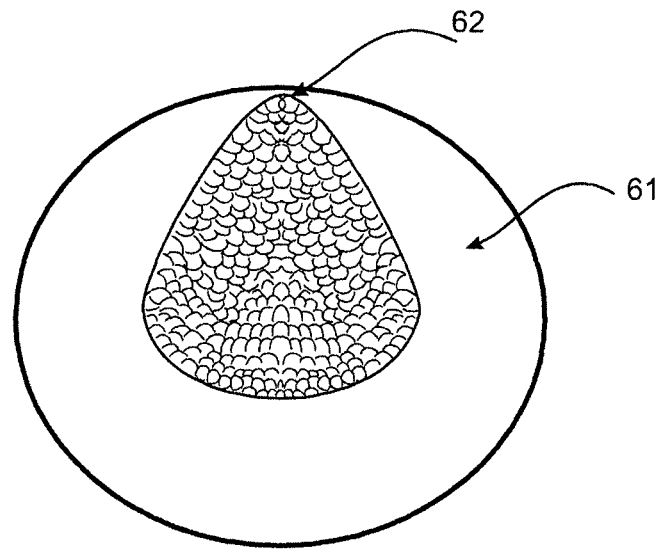
FIG. 7 is a cutaway view of the intragastric balloon of FIG. 1, 2 or 4.

FIG. 7 illustrates a cut away view of the balloon in its expanded state. This embodiment of the balloon is of the spherical form 61, furthermore the cutaway section depicts the reacted cellular foam material 62. The reacted cellular foam material 62 is expanded such that the outer surface of the reacted cellular foam material 62 abuts the inner wall of the balloon.

Figure 8:
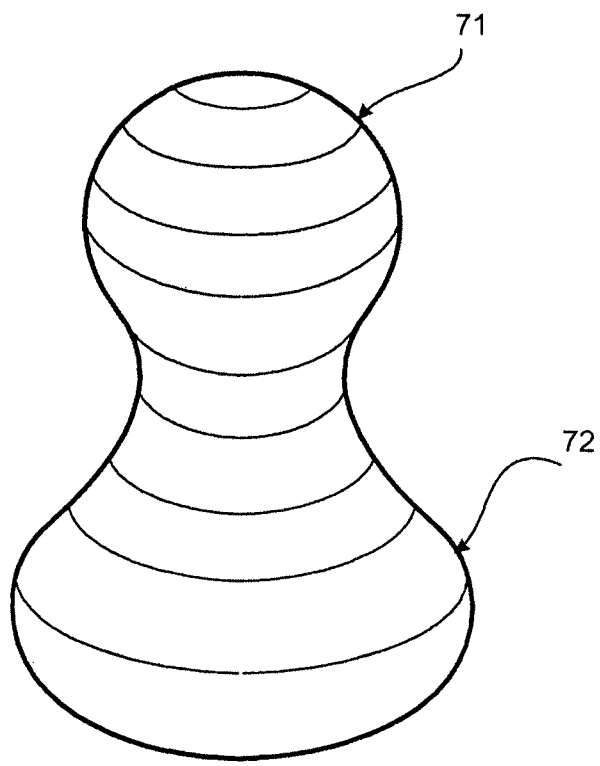
FIG. 8 is a side view of a shape that the intragastric balloon of FIG. 1, 2 or 4 can take when expanded.
Figure 9:
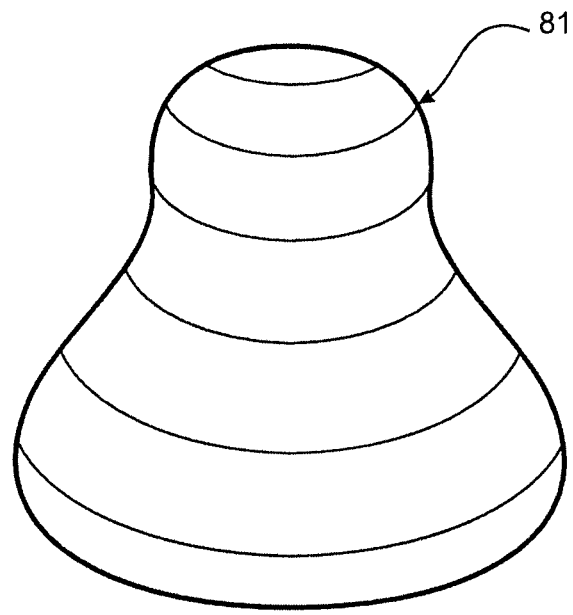
FIG. 9 is a side view of an alternative shape that the intragastric balloon of FIG. 1, 2 or 4 can take when expanded.
Figure 10:
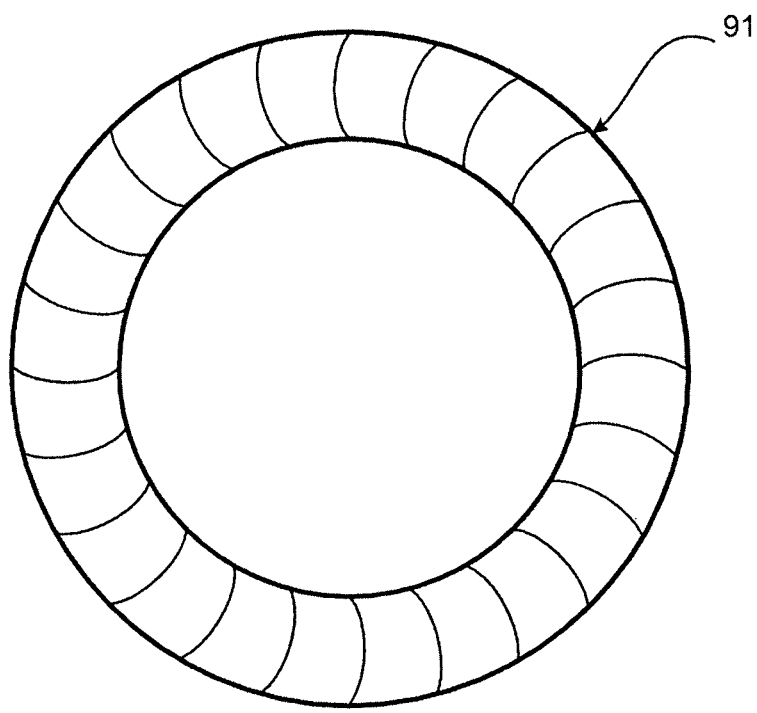
FIG. 10 is a side view of an alternative shape that the intragastric balloon of FIG. 1, 2 or 4 can take when expanded.

FIGS. 8, 9 and 10 illustrate some of the forms the expanded intragastric balloon 810, 910 and 110 can take. FIG. 8 depicts an hourglass shape with two lobes 71 and 72. The hour glass shape can provide stimulation to the proximal region of the stomach to induce the feeling of satiety. FIG. 9 illustrates a pear shape 81 that can also help to stimulate the proximal region of the stomach and induce a feeling of satiety. FIG. 10 illustrates a toroidal form 91 of the balloon designed to occupy maximum volume within the stomach lumen.

Figure 11:
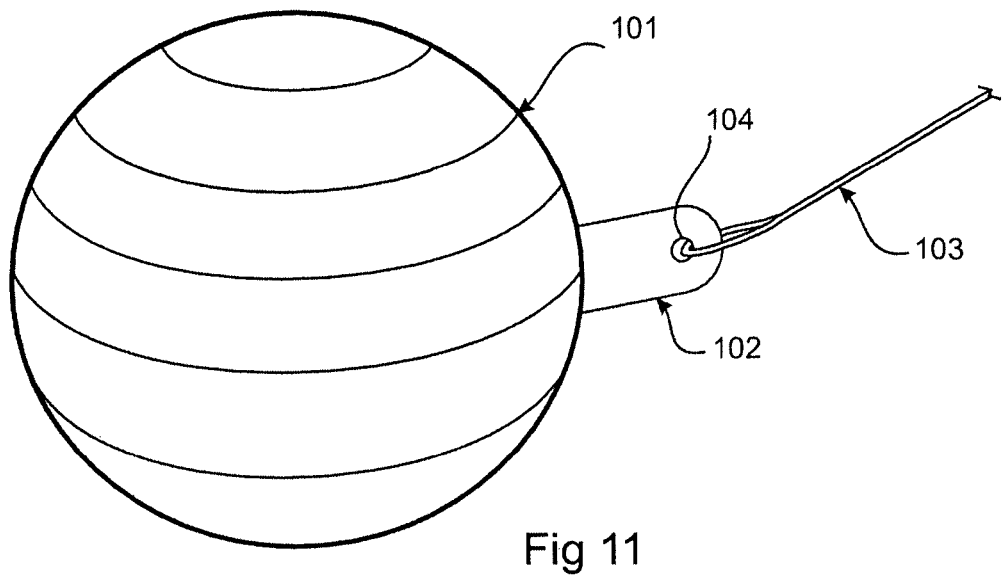
FIG. 11 is a perspective view of a filament attached to the intragastric balloon of FIG. 1, 2 or 4.

FIG. 11 illustrates a spherical form of the intragastric balloon 101 incorporating an additional tab 102. This additional tab 102 can also be attached to any of the other shapes and embodiments of the intragastric balloon discussed. The additional tab 102 can include an aperture 104. The aperture can be used for the attachment of a filament 103. The filament 103 can be attached to the tab 102 prior to insertion of the balloon 101 into the stomach and used in the removal of the balloon 101 if the balloon 101 becomes lodged partway down the oesophagus. The filament 103 can be manufactured from either a digestible or non-digestible material. If a digestible filament 103 is used, once the intragastric balloon 101 has been ingested the filament 103 will break down and release from the primary device. In addition to being useful for the emergency removal during the initial ingestion, the tab 102 can be used to aid in the removal of the balloon 101 after a period of time in the stomach lumen and additionally in the placement of the balloon 101 if the balloon 101 is not ingested.

Figure 12:
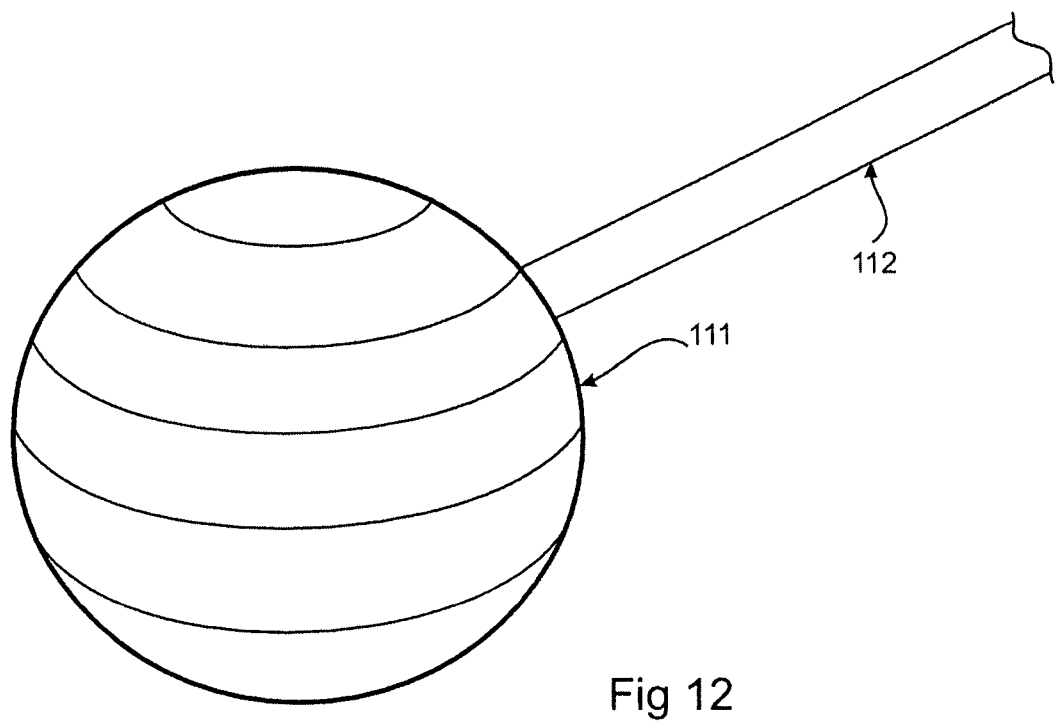
FIG. 12 is a perspective view of a tape attachment attached to the intragastric balloon of FIG. 1, 2 or 4.

FIG. 12 illustrates a spherical form of the intragastric balloon 111 similar to that of FIG. 11 with a tape like member 112 attached, used for the emergency removal of the balloon 111 if the balloon 111 becomes lodged partway down the oesophagus in the same way as the filament 103 discussed above. The tape like member 112 can be attached to any of the embodiments of the intragastric balloon discussed. The tape like member 112 can be manufactured from either a digestible or non-digestible material, the advantage of a digestible member being that once ingested it will break down and release from the primary device.

Figure 13:
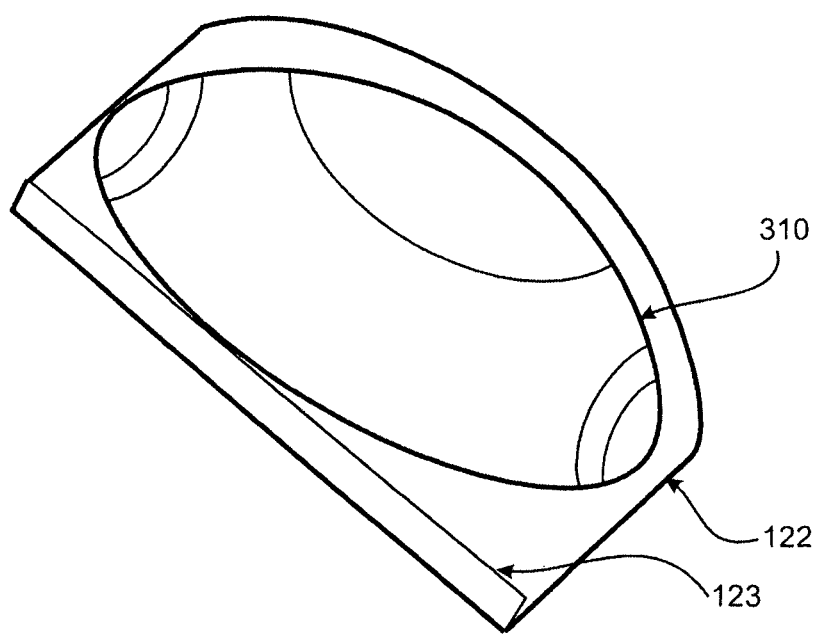
FIG. 13 is a side view of the intragastric balloon of FIG. 1, 2 or 4 held within a pouch.

FIG. 13 illustrates an embodiment of the intragastric balloon 310 prepared for ingestion. The intragastric balloon 310 when compressed through folding, rolling or otherwise may be placed in a pouch 122 to aid the passage of the balloon 310 down the oesophagus. The pouch 122 may have a lip 123 that seals the intragastric balloon 310 within the pouch 122. The pouch 122 can be made of a digestible material and may be lubricated on its outer surface with a suitable biocompatible lubricant to aid passage of the balloon 310 down the oesophagus.

Modifications and variations such as would be apparent to the skilled addressee are considered to fall within the scope of the present invention. The present invention is not to be limited in scope by any of the specific embodiments described herein. These embodiments are intended for the purpose of exemplification only. Functionally equivalent products, formulations and methods are clearly within the scope of the invention as described herein.

Reference to positional descriptions, such as lower and upper, are to be taken in context of the embodiments depicted in the figures, and are not to be taken as limiting the invention to the literal interpretation of the term but rather as would be understood by the skilled addressee.

Throughout this specification, unless the context requires otherwise, the word "comprise" or variations such as "comprises" or "comprising", will be understood to imply the inclusion of a stated integer or group of integers but not the exclusion of any other integer or group of integers.

The invention claimed is:

1. A self-expanding intragastric balloon for use in the stomach, comprising:
   a liquid impermeable intragastric balloon forming a sealed container, wherein the sealed container comprises separated expandable foaming substances;
   wherein the expandable foaming substances are arranged to expand and cure to a foam when mixed; and
   wherein the expanded foam substantially fills the intragastric balloon.

2. The intragastric balloon of claim 1, wherein the intragastric balloon is too large to pass through the pyloric sphincter once the expandable substances are cured.

3. The intragastric balloon of claim 1, wherein the expandable foaming substances are separated by a frangible membrane.

4. The intragastric balloon of claim 1, wherein the expandable foaming substances are separated by an external mechanical separator.

5. The intragastric balloon of claim 1, wherein before the expandable foaming substances have cured the intragastric balloon is adapted to be swallowed.

6. The intragastric balloon of claim 5, wherein the volume of the intragastic balloon before the expandable foaming substances have expanded is between 1 ml and 25 ml.

7. The intragastric balloon of claim 1, wherein the intragastric balloon is adapted to be compressed prior to the expandable foaming substances being cured.

8. The intragastric balloon of claim 7, wherein the intragastric balloon is adapted to be compressed by folding.

9. The intragastric balloon of claim 7, wherein the intragastric balloon is adapted to be compressed by rolling.

10. The intragastric balloon of claim 1, wherein the expandable foaming substances are selected from the following:
    polydimethyl siloxanes;
    polyurethanes; and
    poly siloxanes.

11. The intragastric balloon of claim 1, wherein the sealed container is made from one of the following:
    polydimethyl siloxane;
    polytetrafluro ethylene;
    poly ethylene;
    low density polyethylene;
    poly propolyene;
    polyester; and
    poly amide.

12. The intragastric balloon of claim 1, further comprising a removal device attached to the sealed container adapted to communicate the intragastric balloon with the outside environment when the intragastric balloon is passing into the stomach.

13. The intragastric balloon of claim 1, wherein the volume of the intragastric balloon after the expandable foaming substances have cured is between 50 ml and 700 ml.

14. The intragastric balloon of claim 1, wherein gas transportation of gases produced within the intragastric balloon and atmospheric gases is approximately equal.

15. The intragastric balloon of claim 1, wherein the expandable foaming substances are mixed using a baffle mixer.

16. The intragastric balloon of claim 1, wherein the intragastric balloon is adapted to contain a biocompatible dye within the expandable foaming substances.

17. The intragastric balloon of claim 1, wherein, once the foam has cured, the intragastric balloon is adapted to maintain its shape if punctured.

18. The intragastric balloon as claimed in claim 1, wherein the outer surface of the expanded foam abuts the sealed container.

19. The intragastric balloon of claim 1, wherein the intragastric balloon expands without the use of a tube for passing the foaming substances through the esophagus and into the intragastric balloon.

20. A self-expanding intragastric balloon for use in the stomach, comprising:
    a liquid impermeable intragastric balloon forming a sealed container, wherein the sealed container comprises separated expandable foaming substances;
    wherein the expandable foaming substances are adapted to expand and cure to a foam when mixed, and
    wherein material that the balloon is made of allows transfer, through the material, of the gas created when the mixture expands and cures to a foam so that the foam, when cured, substantially fills the intragastric balloon.

* * * * *